United States Patent [19]

Alisch et al.

[11] Patent Number: 5,472,648
[45] Date of Patent: Dec. 5, 1995

[54] PROCESS AND PLANT FOR THE PRODUCTION OF SPHERICAL ALGINATE PELLETS

[75] Inventors: Gerhard Alisch, Bruchköbel; Edwin Brauneis, Rodenbach; Bernd Pirstadt, Ahorn; Norbert Iffland, Freigericht; Egbert Brandau, Alzenau, all of Germany

[73] Assignee: Nukem GmbH, Alzenau, Germany

[21] Appl. No.: 185,893

[22] PCT Filed: Jul. 22, 1992

[86] PCT No.: PCT/EP92/01670

§ 371 Date: Jun. 13, 1994

§ 102(e) Date: Jun. 13, 1994

[87] PCT Pub. No.: WO93/02785

PCT Pub. Date: Feb. 18, 1993

[30] Foreign Application Priority Data

Jul. 30, 1991 [DE] Germany .................. 41 25 133.4

[51] Int. Cl.6 .................................................. B29B 9/10
[52] U.S. Cl. ................... 264/9; 264/14; 425/6; 425/10
[58] Field of Search ............... 264/4, 5, 9, 14; 425/5, 6, 10

[56] References Cited

U.S. PATENT DOCUMENTS

| 4,795,328 | 3/1989 | Takano | 425/5 |
| 5,021,201 | 6/1991 | Eguchi et al. | 264/9 |

FOREIGN PATENT DOCUMENTS

| 0289648 | 8/1987 | European Pat. Off. . |
| 0268866 | 10/1987 | European Pat. Off. . |
| 0391803 | 4/1990 | European Pat. Off. . |

Primary Examiner—Mary Lynn Theisen
Attorney, Agent, or Firm—Cushman Darby & Cushman

[57] ABSTRACT

Proposed is a process for the production of spherical alginate pellets from drops of alginate solution delivered by a nozzle, the drops being solidified by dropping them into an ionic solution and subsequently removing the pellets and rinsing them. The alginate solution is converted into drops by vibrational stimuli, and the drops subsequently allowed to remain substantially free in the ionic solution until the required degree of solidification has been reached.

12 Claims, 3 Drawing Sheets

PROCESS AND PLANT FOR THE PRODUCTION OF SPHERICAL ALGINATE PELLETS

BACKGROUND OF THE INVENTION

1. Field of the Invention

The invention refers to a method for producing spherical alginate pellets from droplets of an alginate solution delivered from a nozzle, by consolidating the droplets by dropping them into an ion solution, preferably a calcium ion solution, and subsequently washing the alginate pellets removed from the ion solution. The invention further refers to an apparatus for producing spherical alginate pellets from droplets of an alginate solution, comprising a reservoir vessel for the alginate solution; at least one nozzle to which alginate solution can be fed as applicable via a feed line; a collection device, containing an ion solution, for the droplets falling from the nozzle; and at least one device for removing the alginate pellets from the collection device.

Alginate pellets are required, for example, as thickening agents in emulsions, in the cosmetics and food industries, for adhesives and finishes, or as base substances for elastic molding compounds in dentistry, for example. In use, however, the alginate pellets are either completely hardened or only surface-hardened.

Surface-hardened alginate pellets are required, for example, in the cosmetics industry, while completely hardened alginate pellets are required, for example, as supports for enzymes. In order for alginate pellets to be usable to the desired extent, they must be sufficiently pourable and have a narrow particle size spectrum. In particular, a uniform geometry (i.e. a spherical shape) should also be present.

2. Description of the Prior Art

FR-A 2 645 439 has disclosed a method for producing spherical alginate pellets intended for the cosmetics industry, according to which an alginate solution is fed to a nozzle from which the alginate solution is delivered in droplet form, subsequently falling into a calcium ion solution. Located in the calcium ion solution is an endless-loop conveyor belt by which the droplets are collected and then transported out of the calcium ion solution.

Since there is no assurance that the droplets are surface-hardened to a sufficient extent as they fall through the calcium ion solution, the alginate pellets removed from the calcium ion solution by the conveyor belt are often flattened. Since the droplets form simply by dripping alginate solution out of the nozzle, a desirable narrow particle size spectrum also cannot be achieved.

SUMMARY OF THE INVENTION

The underlying problem of the present invention is to develop a method and an apparatus of the aforesaid type for producing spherical alginate pellets in such a way that, among other effects, alginate pellets with a spherical geometry and a narrow particle size spectrum are obtained, and that hardening of the alginate pellets themselves can be adjusted in a controlled manner.

According to the invention, the problem is solved in terms of the method by the fact that the alginate solution is formed into drops by vibratory excitation, and that until they achieve the desired consolidation, the droplets are initially, until surface hardening occurs, substantially free to move in the ion solution. In this connection an "ion solution" is understood to mean an ionic solution whose metal ions combine with alginate to form a poorly soluble compound. Preferably the ion solution can be a calcium ion solution.

In contrast to the prior art, the alginate solution is not dripped, but rather formed into drops by the nozzle, which itself can be excited to vibrate. This is not, however, a mandatory feature. Instead vibratory excitation can also occur by exciting the alginate solution in a reservoir container or by acoustic irradiation of the alginate solution itself.

Regardless of the kind of vibratory excitation, however, it is essential that a constant frequency act on the alginate solution, with rotationally symmetrical constrictions being generated and reinforced in a stream of liquid leaving the nozzle, so that uniform disintegration into droplets, called "dropletization," occurs. This ensures that the droplets have identical or almost identical sizes, so that as a result, the alginate pellets produced have a narrow particle size spectrum.

While dropletization ensures the narrow particle size spectrum, the feature by which the droplets remain free to move for so long within a precipitation solution (i.e. the ion solution)—in other words can move freely without striking masses that are large by comparison with the alginate mass—guarantees that the droplets are not deformed while hardening, and that consequently the final geometry of the alginate pellets exhibits a spherical geometry. In this connection the residence time in the alginate solution can be adjusted in a controlled manner so that consolidation can be performed reproducibly.

According to a development of the invention, the droplets can fall under their own weight through an ion solution column until the desired consolidation occurs. It is also possible, however, to define the residence time of the droplets in the ion solution by means of the flow velocity of the solution in which the droplets are moving.

A further proposal of the invention worth emphasizing provides for the droplets, before contacting the precipitation solution, to be intercepted on a foam present thereon, which can have a thickness of, for example, 5–50 mm. The droplets are decelerated while falling through the foam, so that when they subsequently contact the surface of the precipitation solution, flattening of the alginate droplets is largely ruled out.

To reduce the surface tension of the precipitation solution even further, a surfactant or an organic solvent, preferably an alcohol such as ethanol, propanol, etc., can be added thereto.

An apparatus for producing alginate droplets is characterized by the fact that the apparatus for dropletizing the alginate solution delivered by the nozzle has a vibration exciter, and that the collection device has a liquid column of the ion solution of a length such that the droplets can be consolidated to the desired extent while flowing through the liquid column. A liquid column in this case is not necessarily to be understood as, for example, a tubular reactor (plug flow reactor) in the shape of a tube or hose containing the precipitation solution, with which the exact residence time of the alginate droplets or pellets in the precipitation solution can be adjusted and varied to the desired degree. The term "liquid column" very generally denotes a quantity of liquid which offers the alginate droplets dropping into the precipitation solution the opportunity not to come into contact with masses that are large by comparison with the alginate droplets before the desired hardening, especially surface hardening, has occurred. Thus a batch reactor with or without a stirrer (for complete hardening of the alginate pellets) can also be utilized.

A mechanical vibrator, magnetic-induction vibrator, pneumatic vibrator, piezoelectric converter, or electroacoustic converter can be used as the vibration exciter; the vibration exciter can act on the nozzle and/or on the feed line and/or on the reservoir container. It is also possible to acoustically irradiate the alginate solution directly, for example with an electroacoustic converter, or to excite it directly with a vibrating displacer or plunger, in order to dropletize the stream of alginate solution emerging from the nozzle into uniform droplets.

Preferably the ion solution, which is preferably a $CaCl_2$ solution, has a surfactant or organic solvent added to it in order to reduce the surface tension of the precipitation solution.

To greatly reduce the "impact" of the alginate droplets on the surface of the precipitation solution, a foam layer, which itself is a foamed solution of surfactant or organic solvent, can be formed on the ion solution. The height of this foam layer is preferably between 5 and 50 mm.

The frequency acting on the apparatus or the alginate solution must be kept constant during the production process, with excitation frequencies of between 50 and 20,000 Hz preferably being used. The viscosity of the alginate solution should be less than 200 mPa×s. Lastly, the diameter of the nozzle should fall in the range between 50 and 3000 µm.

With these parameters, spherical alginate pellets of uniform geometrical configuration with a narrow particle size spectrum can be generated; depending on frequency and nozzle diameter, alginate pellet diameters of between 100 and 4000 um can be achieved.

Further details, advantages, and features of the invention are evident not only from the Claims [and] the features evident from them—individually and/or in combination— but also from the description below of preferred exemplary embodiments presented in the drawings, in which:

DESCRIPTION OF THE PREFERRED EMBODIMENT

Figure 1:
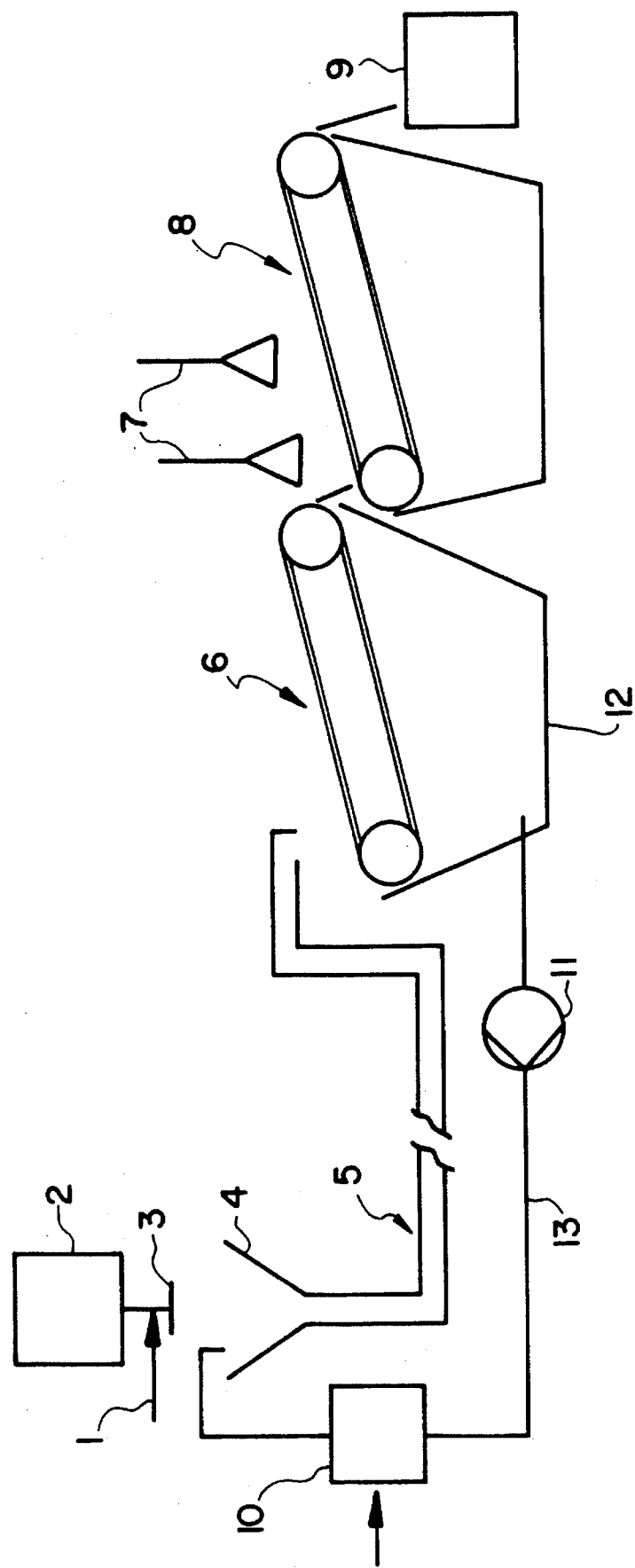
FIG. 1 shows a schematic depiction of an apparatus for producing spherical alginate pellets.

In FIG. 1, reference number (1) designates a system for feeding and metering an alginate solution that is delivered via a nozzle (3) into a collection device (4) which contains an ion solution, preferably in the form of 2% $CaCl_2$ in deionized water.

In order for the alginate solution delivered by the nozzle (3) to dropletize, i.e. in order to obtain alginate solution droplets of reproducible size, a vibration exciter system that is indicated purely schematically and given the reference number (2) is provided. This exciter system can act directly on the nozzle (3) and cause it to vibrate horizontally or vertically. It is also possible to impress vibrations on the feed line (1). Alternatively, it is possible to excite the alginate solution present in a reservoir container. Lastly, the stream of alginate solution leaving the nozzle (3) can also be acoustically irradiated.

Potential vibration exciters include magnetic-induction vibrators, mechanical vibrators, pneumatic vibrators, piezoelectric converters, and electroacoustic converters.

In the schematic depiction according to FIG. 1, the alginate droplets fall from the collection device (4)—in which a foam layer of a surfactant solution, with a height of, for example, 5–50 mm, can be present on the ion solution— through a tubular reactor (5); inside the tubular reactor (5), the alginate droplets are to be free to move at least until surface consolidation has occurred. Under these conditions the alginate droplets have the desired spherical geometry, so that a collision with other alginate droplets or pellets, or with the walls of the tubular reactor (5), will cause no further deformation.

After leaving the tubular reactor, the alginate pellets, consolidated to the desired degree, are delivered onto a traveling screen (6), from which the calcium chloride solution remaining on the alginate pellets drips off. From the traveling screen (6) the alginate pellets pass onto a traveling screen (8), on which they are washed using wash water nozzles (7). From the traveling screen (8) the alginate pellets are collected as finished products in a collection device (9), and then passed on to their desired application.

The ion solution flows through the tubular reactor (5) at a desired velocity. The residence time of the alginate droplets or pellets in the ion solution is determined by the velocity of the ion solution and the length of the tubular reactor, so that they can be consolidated reproducibly to the desired degree. The ion solution is conveyed by means of a pump (11) through a circuit which comprises a connection (13) from a collection container (12) present beneath the traveling screen (6) to the collection device (4). Also located in the connection or line (13) is a flow concentration controller (10) for the ion solution.

Figure 2:
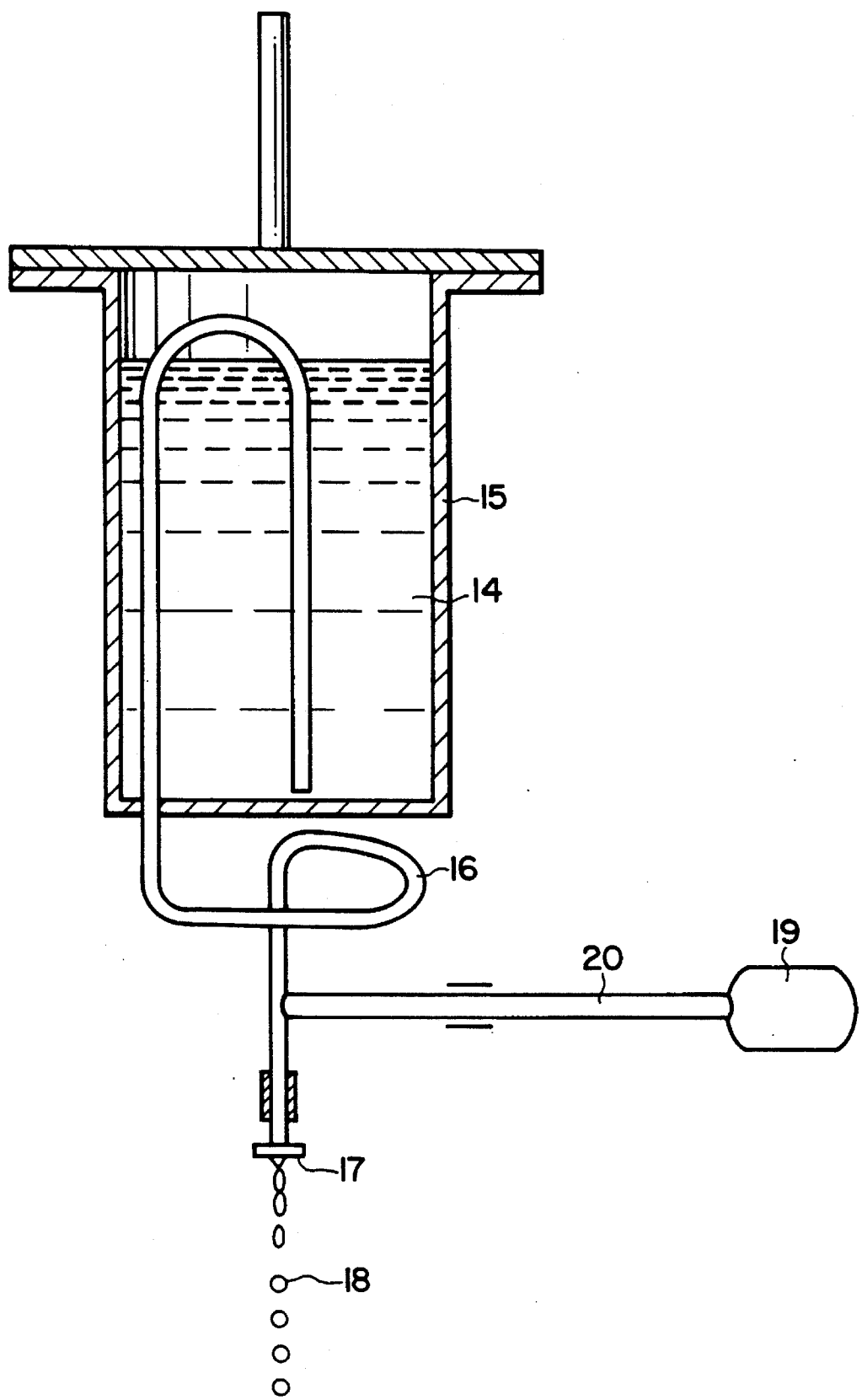
FIG. 2 shows a first exemplary embodiment of an apparatus for producing droplets of an alginate solution.

FIG. 2 depicts a section of an apparatus for producing spherical alginate pellets, specifically that with which droplets are produced from the alginate solution. The alginate solution (14) is located in a reservoir vessel (15) from which the alginate solution (14) is fed via a feed line (16) to a nozzle (17), from which the alginate solution (14) falls under its own weight in the form of droplets (18). It is evident that directly below the nozzle (17) the droplets have an elongated shape; after they have fallen a certain distance this changes into a spherical shape due to the surface tension of the alginate solution.

A vibration generator (19), which is connected directly or indirectly to the nozzle (17) via a rigid connection (20), generates a vibration which causes dropletization of the alginate solution leaving the nozzle (17), i.e. rotationally symmetrical constrictions are generated and reinforced in the stream of liquid leaving the nozzle (17), causing disintegration into uniform droplets.

Figure 3:
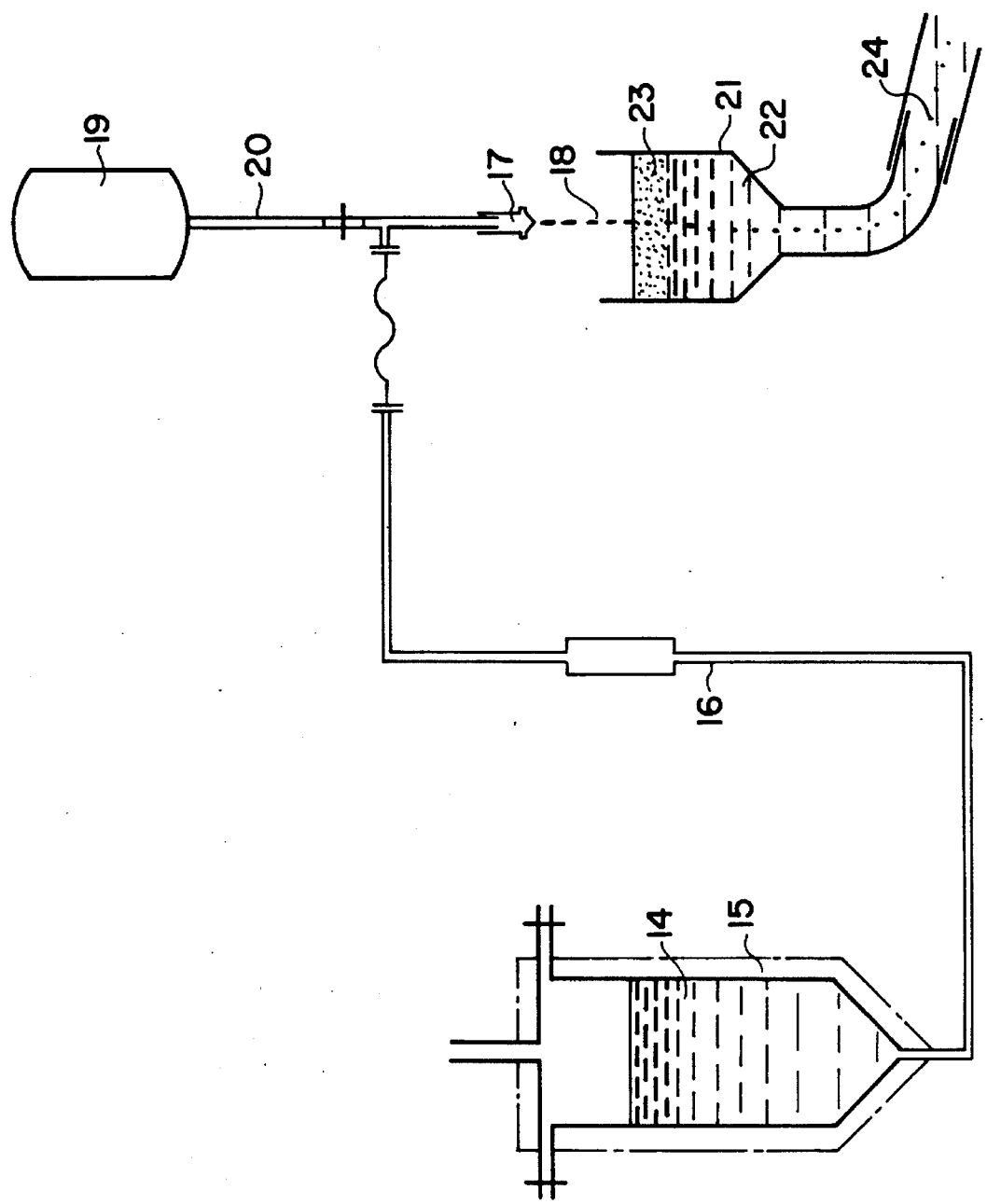
FIG. 3 shows a second embodiment of an apparatus for producing droplets from an alginate solution.

Although according to the exemplary embodiment of FIG. 2 the alginate solution (14) is fed to the nozzle (17) by gravity, according to the exemplary embodiment of FIG. 3 a pressure delivery system is provided. Otherwise the configuration of FIG. 3 corresponds to that of FIG. 2, and identical elements are therefore also given identical reference numbers.

Additionally depicted is a collection device (21) in which, for example, a calcium chloride solution is present or through which it flows. Located above the liquid level of the calcium chloride solution is a foam layer (23) of a surfactant solution, which "decelerates" the droplets (18). The resulting advantage is that when the droplets (18) strike the liquid surface of the calcium chloride solution, undesired flattening is largely eliminated.

The droplets (18) that fall or are conveyed through the solution are initially consolidated externally by reaction with the calcium chloride solution, so that alginate pellets (24) of a desired consolidation are present within the chloride solution (22); as mentioned, consolidation depends on the residence time of the alginate pellets in the calcium chloride solution (22).

The reactor (21) containing the calcium chloride or precipitation solution can—as in the exemplary embodiment of FIG. 1—be a tubular reactor with which the exact residence time of the alginate pellets (24) in the precipitation solution can be adjusted by varying the reactor length and the flow velocity of the precipitation solution, thus generating alginate pellets (24) that [have] a desired consolidation, i.e. can be hardened only at the surface or completely hardened.

The reactor can also be a batch reactor which may possibly have a stirrer, especially if the alginate pellets (24) are to be completely hardened.

With regard to the precipitation solution, it should also be noted that a surfactant or organic solvent can be added to it in order to reduce the surface tension. As described with reference to FIG. 3, a foam of surfactant or organic solvent can also be present on the precipitation solution (22). It is also possible to take the precipitation solution (22) from a receiving device with an overflow channel.

The nozzle used to dropletize the alginate solution can be a full-flow nozzle made of various materials. It is also possible to use a nozzle plate, namely one with a plurality of nozzles.

The alginate solution used in the method according to the invention should have a viscosity less than 200 mPa×s. The excitation frequency with which the solution emerging from the nozzle is dropletized should be between 50 and 20,000 Hz. The nozzle diameter itself can lie in the range between 50 and 3000 μm. When these parameters are observed, alginate pellet diameters in the range between 100 and 4000 μm, with an almost exactly spherical shape, can be obtained. The respective alginate pellets produced under identical parameters have a very narrow particle size spectrum.

The examples below indicate further advantages and features of the invention, which—individually or in combination—are to be regarded as inventive.

EXAMPLE 1

A reservoir vessel (15) contains an alginate solution that is fed to the nozzle (17) with a diameter of 280 μm, which in turn is caused to vibrate at a frequency of 2100 Hz. The dropletized alginate solution falls into a calcium ion solution, specifically into 2% CaCl2 in deionized water. The alginate droplets or pellets remain in the precipitation solution for 30 minutes, resulting in complete hardening. The diameter of the resulting spherical pellets is 500 μm, with a standard deviation of approximately 1%. No foam was present on the precipitation solution itself.

EXAMPLE 2

To obtain surface-hardened alginate pellets, a tubular reactor containing a precipitation solution in the form of 0.35% $CaCl_2$ plus 0.05% surfactant and deionized water is used. The nozzle with which the alginate solution is dropletized has a diameter of 900 μm. The vibration frequency is 155 Hz. The alginate pellets remain in the precipitation solution for 1 minute. As a result, alginate pellets with a hardened surface and a diameter of 1700 μm are obtained. In this case as well, the standard deviation is 1%.

EXAMPLE 3

Once again a tubular reactor is used, containing a precipitation solution with the following composition: 0.26% $CaCl_2$ plus 0.05% surfactant in deionized water. The nozzle used has a diameter of 1925 μm. The frequency is 50 Hz. A surfactant foam approximately 20 mm high is present on top of the precipitation solution. The alginate pellets remain in the precipitation solution for 1.5 minutes. As a result, surface-hardened alginate pellets with diameters of 3400 μm are obtained. Standard deviation is 1%.

EXAMPLE 4

A processing sequence corresponding to that of Example 3 is performed, but instead of 0.05% surfactant, 8% isopropyl alcohol is added to the $CaCl_2$ solution. The alginate pellets produced in this manner also have the desired properties in terms of surface hardening and diameter (3400 μm with a standard deviation of 1%).

We claim:

1. Method for producing spherical alginate pellets from droplets of an alginate solution delivered from a nozzle, by consolidating the droplets by dropping them into an ion solution and subsequently washing the alginate pellets removed from the ion solution, wherein the alginate solution is dropletized by vibratory excitation;

the droplets are substantially free to move in the ion solution until they achieve the desired consolidation; and before contacting the ion solution, the droplets are decelerated by a foam present thereon, and/or the droplets fall into the ion solution whose surface tension has been reduced by a surfactant or an organic solvent.

2. Method according to claim 1 wherein the alginate solution is dropletized by vibratory excitation and the droplets are substantially free to move in the ion solution until they achieve the desired consolidation, the residence time of the droplets in the ion solution being dependent substantially on the flow velocity of the ion solution and the length of ion solution through which the droplets flow.

3. Method according to claim 1 wherein the droplets are substantially free to move in the ion solution at least until they achieve surface hardening.

4. Method according to claim 2 wherein the droplets are substantially free to move in the ion solution at least until they achieve surface hardening.

5. Method according to claim 1 wherein the droplets fall under their own weight through an ion solution column until the desired consolidation occurs.

6. Method according to one of claims 1–5 wherein the nozzle and/or the alginate solution and/or a reservoir container receiving the alginate solution and/or a feed line feeding the alginate solution to the nozzle is caused to vibrate.

7. Apparatus for producing spherical alginate pellets from droplets of an alginate solution (14), comprising a reservoir container (15) for the alginate solution; at least one nozzle (3, 17) to which alginate solution can be fed as applicable via a feed line (16, 20); a collection device (4, 21), containing an ion solution for the droplets falling from the nozzle; and at least one device for removing the alginate pellets from the collection device (6, 7, 8, 9), wherein the apparatus for dropletizing the alginate solution (14) delivered by the nozzle (3, 17) has a vibration exciter (2, 19); and the collection device (4, 5, 21) is a tubular reactor through which the ion solution (22) can flow in an adjustable manner, with a liquid column such that the droplets (18) can be consolidated at least on their surfaces wile flowing through the liquid column.

8. Apparatus according to claim 7, wherein the vibration exciter is a mechanical or magnetic-induction vibrator, a pneumatic vibrator, a piezoelectric converter or electroacoustic converter, or a vibrating displacer/plunger.

9. Apparatus according to claim 7, wherein the vibration exciter (2, 19) acts on the nozzle (3, 17) and/or on the feed line (1, 16) and/or on the reservoir container (15) or on the interior of the nozzle.

10. Apparatus according to claim 8, wherein the vibration exciter (2, 19) acts on the nozzle (3, 17) and/or on the feed line (1, 16) and/or on the reservoir container (15) or on the interior of the nozzle.

11. Apparatus according to claim 7, further comprising a means by which the alginate solution (14) can be acoustically irradiated.

12. Apparatus according to one of claims 7–11 wherein the ion solution contains $Ca^{2+}$ ions or one or more other ion species that form a poorly soluble compound with alginate.

* * * * *